(12) United States Patent
Giambattista et al.

(10) Patent No.: US 7,666,164 B2
(45) Date of Patent: Feb. 23, 2010

(54) PEN NEEDLE AND SAFETY SHIELD SYSTEM

(75) Inventors: Lucio Giambattista, East Hanover, NJ (US); David E. DeSalvo, Butler, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 11/006,497

(22) Filed: Dec. 7, 2004

(65) Prior Publication Data

US 2005/0283115 A1    Dec. 22, 2005

Related U.S. Application Data

(63) Continuation of application No. 10/072,691, filed on Feb. 7, 2002, now abandoned.

(60) Provisional application No. 60/222,454, filed on Aug. 2, 2000.

(30) Foreign Application Priority Data

Jul. 25, 2001    (WO) ................. PCT/US01/23367

(51) Int. Cl.
*A61M 5/00* (2006.01)
(52) U.S. Cl. .................. 604/110; 604/192; 604/198
(58) Field of Classification Search .................. 604/110, 604/130–137, 192–198, 181, 187; 128/218
See application file for complete search history.

(56) References Cited

U.S. PATENT DOCUMENTS

| | | | |
|---|---|---|---|
| 2,752,918 A | 7/1956 | Uytenbogaar | |
| 3,712,301 A | 1/1973 | Sarnoff | |
| 3,882,863 A | 5/1975 | Sarnoff et al. | |
| 4,031,893 A | 6/1977 | Kaplan et al. | |
| 4,214,584 A | 7/1980 | Smirnov et al. | |
| 4,226,235 A | 10/1980 | Sarnoff et al. | |
| 4,413,760 A | 11/1983 | Paton | |
| 4,565,543 A | 1/1986 | Bekkering et al. | |
| 4,624,660 A | 11/1986 | Mijers et al. | |
| 4,755,169 A | 7/1988 | Sarnoff et al. | |

(Continued)

FOREIGN PATENT DOCUMENTS

WO    WO 9219296    11/1992

(Continued)

*Primary Examiner*—Kevin C. Sirmons
*Assistant Examiner*—Phillip Gray
(74) *Attorney, Agent, or Firm*—Alan W. Fiedler

(57) ABSTRACT

A safety shield system for a needle cannula of a pen needle injector or similar device, wherein the safety shield may be retracted from a first position enclosing the needle to a second position exposing the needle for injection. The safety shield system permits retraction of the safety shield during use, but extends the shield enclosing the needle in a locked position following use. The shield system is utilized with a pen needle injector having a double ended needle cannula mounted in a hub received on the open end of the pen needle injector. The assembly is disposed of by removing the assembly and needle cannula hub and storing the assembly in the cup-shaped cap enclosing the exposed end of the needle cannula within the cap. The cap includes internal radial ribs preventing retraction of the shield prior to removing the cap preventing inadvertently piercing the cap during assembly.

25 Claims, 7 Drawing Sheets

U.S. PATENT DOCUMENTS

| | | | |
|---|---|---|---|
| 4,801,295 A * | 1/1989 | Spencer | 604/198 |
| 4,822,340 A | 4/1989 | Kamstra | |
| 4,894,055 A * | 1/1990 | Sudnak | 604/198 |
| 4,911,693 A * | 3/1990 | Paris | 604/192 |
| 4,968,302 A | 11/1990 | Schluter et al. | |
| 5,017,190 A | 5/1991 | Simon et al. | |
| 5,085,641 A | 2/1992 | Sarnoff et al. | |
| 5,085,642 A | 2/1992 | Sarnoff et al. | |
| 5,104,380 A | 4/1992 | Holman et al. | |
| 5,112,317 A | 5/1992 | Michel | |
| 5,169,392 A | 12/1992 | Ranford et al. | |
| 5,201,708 A | 4/1993 | Martin | |
| 5,201,721 A | 4/1993 | Lee et al. | |
| 5,226,895 A | 7/1993 | Harris | |
| 5,226,896 A | 7/1993 | Harris | |
| 5,244,465 A | 9/1993 | Michel | |
| 5,279,585 A | 1/1994 | Balkwill | |
| 5,279,586 A | 1/1994 | Balkwill | |
| 5,295,976 A | 3/1994 | Harris | |
| 5,300,030 A | 4/1994 | Crossman | |
| 5,304,152 A | 4/1994 | Sams | |
| D347,894 S | 6/1994 | Hansel et al. | |
| 5,358,489 A | 10/1994 | Wyrick | |
| 5,383,865 A | 1/1995 | Michel | |
| 5,385,551 A | 1/1995 | Shaw | |
| 5,391,151 A | 2/1995 | Wilmot | |
| 5,403,286 A | 4/1995 | Lockwood, Jr. | |
| 5,415,645 A | 5/1995 | Friend et al. | |
| 5,417,660 A | 5/1995 | Martin | |
| 5,417,662 A | 5/1995 | Hjertman et al. | |
| 5,429,612 A | 7/1995 | Berthier | |
| 5,478,316 A * | 12/1995 | Bitdinger et al. | 604/135 |
| 5,480,387 A | 1/1996 | Gabriel et al. | |
| 5,514,097 A | 5/1996 | Knauer | |
| 5,540,664 A | 7/1996 | Wyrick | |
| 5,545,145 A | 8/1996 | Clinton et al. | |
| 5,549,558 A | 8/1996 | Martin | |
| 5,569,192 A | 10/1996 | van der Wal | |
| 5,584,815 A | 12/1996 | Pawelka et al. | |
| 5,593,390 A | 1/1997 | Castellano et al. | |
| 5,620,421 A | 4/1997 | Schmitz | |
| 5,626,566 A | 5/1997 | Petersen et al. | |
| 5,634,910 A | 6/1997 | Kanner et al. | |
| 5,637,094 A | 6/1997 | Stewart, Jr. et al. | |
| 5,645,534 A | 7/1997 | Chanoch | |
| 5,658,259 A | 8/1997 | Pearson et al. | |
| 5,665,071 A | 9/1997 | Wyrick | |
| 5,674,203 A | 10/1997 | Lesandowski | |
| 5,679,111 A | 10/1997 | Hjertman et al. | |
| 5,688,251 A | 11/1997 | Chanock | |
| 5,693,027 A | 12/1997 | Hansen et al. | |
| 5,695,472 A | 12/1997 | Wyrick | |
| 5,709,662 A * | 1/1998 | Olive et al. | 604/135 |
| 5,725,508 A | 3/1998 | Chanock et al. | |
| 5,728,074 A | 3/1998 | Castellano et al. | |
| 5,746,727 A | 5/1998 | Graves et al. | |
| 5,820,602 A | 10/1998 | Kovelman et al. | |
| 5,827,232 A | 10/1998 | Chanock et al. | |
| 5,829,589 A | 11/1998 | Nguyen et al. | |
| 5,836,911 A | 11/1998 | Marzynski et al. | |
| 5,843,036 A * | 12/1998 | Olive et al. | 604/136 |
| 5,873,462 A | 2/1999 | Nguyen et al. | |
| 5,873,856 A | 2/1999 | Hjertman et al. | |
| 5,893,845 A | 4/1999 | Newby et al. | |
| 5,928,205 A | 7/1999 | Marshall | |
| 5,938,642 A | 8/1999 | Burroughs et al. | |
| 5,941,857 A | 8/1999 | Nguyen et al. | |
| 5,944,700 A | 8/1999 | Nguyen et al. | |
| 5,951,530 A | 9/1999 | Steengaard et al. | |
| 5,957,896 A | 9/1999 | Bendek et al. | |
| 5,961,495 A | 10/1999 | Walters et al. | |
| 5,964,731 A | 10/1999 | Kovelman | |
| 5,968,021 A | 10/1999 | Ejersen | |
| 5,971,966 A | 10/1999 | Lav | |
| 5,980,491 A | 11/1999 | Hansen | |
| 5,984,900 A | 11/1999 | Mikkelsen | |
| 5,984,906 A | 11/1999 | Bonnichsen et al. | |
| 6,001,082 A | 12/1999 | Dair et al. | |
| 6,001,089 A | 12/1999 | Burroughs et al. | |
| 6,004,297 A | 12/1999 | Steenfeldt-Jensen et al. | |
| 6,017,329 A * | 1/2000 | Hake | 604/198 |
| 6,039,713 A | 3/2000 | Btoich et al. | |
| 6,048,336 A | 4/2000 | Gabriel | |
| 6,056,728 A | 5/2000 | von Schuckmann | |
| 6,077,247 A | 6/2000 | Marshall | |
| 6,077,253 A | 6/2000 | Cosme | |
| 6,090,080 A | 7/2000 | Jost et al. | |
| 6,093,172 A | 7/2000 | Funderburk et al. | |
| 6,110,149 A | 8/2000 | Klitgaard et al. | |
| 6,126,194 A | 10/2000 | Yaniv et al. | |
| 6,126,646 A | 10/2000 | Hansen et al. | |
| 6,159,181 A | 12/2000 | Crossman et al. | |
| 6,162,197 A | 12/2000 | Mohammad | |
| 6,193,698 B1 | 2/2001 | Kirchhofer et al. | |
| 6,203,529 B1 | 3/2001 | Gabriel et al. | |
| 6,221,046 B1 | 4/2001 | Burroughs et al. | |
| 6,221,053 B1 | 4/2001 | Walters et al. | |
| 6,241,709 B1 | 6/2001 | Bechtold et al. | |
| 6,248,095 B1 | 6/2001 | Giambattista et al. | |
| 6,277,097 B1 | 8/2001 | Mikkelsen et al. | |
| 6,277,099 B1 | 8/2001 | Stowe et al. | |
| 6,277,101 B1 | 8/2001 | Kirchhofer et al. | |
| 6,319,225 B1 | 11/2001 | Sugita et al. | |
| 6,322,540 B1 | 11/2001 | Grabis et al. | |
| 6,379,337 B1 | 4/2002 | Mohommad | |
| 6,547,764 B2 | 4/2003 | Larsen et al. | |
| 6,569,123 B2 | 5/2003 | Alchas et al. | |
| 6,773,415 B2 | 8/2004 | Heiniger | |
| 6,986,760 B2 | 1/2006 | Giambattista et al. | |
| 7,074,211 B1 | 7/2006 | Heiniger et al. | |
| 2001/0005781 A1 | 6/2001 | Bergens et al. | |
| 2001/0009990 A1 | 7/2001 | Hostettler et al. | |
| 2001/0020155 A1 | 9/2001 | Mikkelsen et al. | |
| 2001/0051792 A1 | 12/2001 | Kirchhofer et al. | |
| 2002/0004648 A1 | 1/2002 | Larsen et al. | |
| 2002/0010422 A1 | 1/2002 | Du Plessis | |
| 2005/0283115 A1 | 12/2005 | Giambattista et al. | |

FOREIGN PATENT DOCUMENTS

| | | |
|---|---|---|
| WO | 92/19296 | 12/1992 |
| WO | 97/14455 | 4/1997 |
| WO | WO 9714455 | 4/1997 |
| WO | 02/09797 | 2/2002 |
| WO | WO 0209797 | 2/2002 |

* cited by examiner

PEN NEEDLE AND SAFETY SHIELD SYSTEM

CROSS-REFERENCE TO RELATED APPLICATIONS

This application is a Continuation of U.S. patent application Ser. No. 10/072,691, filed on Feb. 7, 2002, now abondoned which claims priority to PCT Application No. PCT/US01/23367 filed Jul. 25, 2001, which claims priority to U.S. Provisional Application No. 60/222,454 filed Aug. 2, 2000.

FIELD AND BACKGROUND OF THE INVENTION

The present invention relates to an improved pen needle and safety shield system particularly, but not exclusively, adapted for pen injectors. The safety shield system of this invention includes a retractable generally tubular shield which is spring biased to normally enclose the needle cannula of a pen needle dispenser, but which locks in the extended position enclosing the needle cannula following injection. Further, the double ended needle cannula assembly may be safely nested in the cup-shaped cap following injection for disposal.

Hypodermic syringes have been used for many years to deliver selected doses of fluids including liquid medicaments, inoculations, etc. to patients. However, many applications using hypodermic needles are self-administered, including, for example, insulin, anti-histamines, et cetera. The required manipulation of a standard prior art hypodermic syringe can be inconvenient, particularly where the injection is self-administered in a public environment. Medication delivery pens or pen injectors have therefore been developed to facilitate self-administration of injections. A typical pen injector includes a generally tubular body portion resembling a fountain pen which receives a vial of fluid, such as insulin, antihistamines, et cetera, having a pierceable closure, such as a rubber septum. The pen needle includes a hub generally having a double ended needle cannula including a first end which extends into the body portion of the pen injector for piercing the closure of the vial and a second end used for self-injection of the fluid contained in the vial. The pen needle also generally includes a removable cup-shaped cap which encloses the second end of the needle cannula prior to use.

Various improvements in pen needles have been developed or proposed by the prior art since its introduction, including adjustable injection length pen needles as disclosed in U.S. Pat. No. 5,944,700 assigned to the assignee of the present application and safety shield systems for such pen needles, wherein the shield is generally cup-shaped including an open end which receives the body portion of the pen needle and a generally closed end portion having a central opening which receives the second end of the needle cannula when the shield is retracted from a first position enclosing the second end of the needle cannula to a second position wherein the needle cannula is exposed for injection. The assembly may further include a spring that biases the shield to the normally enclosed first position prior to injection.

Various safety shield systems have also been developed or proposed by the prior art for conventional hypodermic syringes wherein a tubular shield is spring biased to enclose the needle cannula following injection and including safety shields which lock in the extended enclosed position following injection. Such safety shield systems for conventional hypodermic syringes are operated manually or are spring biased to extend the tubular shield and enclose the needle cannula following injection but all require additional action (active systems,) such as force, to activate as compared to the standard injection process. Hand manipulated safety shield systems may include spiral or complicated channel-shaped tracks on an inside surface of the shield which guide the shield during extension of the shield to enclose the needle cannula and lock the shield in the extended position. However, such complicated track systems may not always be reliable.

A safety shield system for pen needles has not yet been developed wherein the shield initially encloses the second end of the needle cannula prior to use, permits retraction of the shield for self-administration of the fluid in the pen needle dispenser and then extends and locks the shield in the extended position enclosing the needle cannula following use. It would also be desirable to simplify the operation of the shield to eliminate manual manipulation or rotational movement of the shield from the retracted position to a locked extended position.

One problem with other pen needle accessories, such as hidden needle adapters, has been potential needle sticks to the user during assembly of the accessory on the pen injector. Because the shield must be retractable for injection and the shield and cap assembly is typically threaded on the pen needle dispenser, the natural tendency of the user or patient is to press the cap toward the injector during assembly. This may cause the needle to pierce the cap and possibly puncture the user during assembly. Another problem associated with pen needles has been the safe disposal of the hub and double ended needle cannula. It would be most desirable to safely enclose both sharp ends of the needle cannula hub assembly to avoid inadvertent punctures during and following disposal. As will be understood, one end of the needle cannula may be enclosed in the cup-shaped cap; however, the other end is exposed following removal of the hub assembly from the pen injector.

The pen needle and safety shield system of this invention solves these problems by providing a safety shield which normally encloses the needle cannula prior to use, permits retraction of the safety shield during injection and automatically extends and locks the shield in the extended enclosed position following use. The pen needle of this invention also prevents retraction of the shield during assembly of the shield and needle cannula and hub assembly on the pen injector. Further, the improved safety shield system of this invention permits safe disposal of the hub and double-ended needle cannula assembly following removal from the pen injector.

SUMMARY OF THE INVENTION

As set forth above, the improved safety shield system of this invention is particularly but not exclusively adapted for pen injectors. That is, although the safety shield system of this invention was specifically designed for use with pen injectors of the type described herein, the safety shield system of this invention may also be used with other devices including conventional hypodermic needle fluid delivery systems. For ease of description, however, the safety shield system of this invention will now be described as a component of a pen injector. As set forth above, such pen injectors generally include a tubular body portion adapted to receive a conventional vial for dispensing a fluid, such as insulin, anti-histamines, et cetera. A conventional pen needle dispenser further includes a needle cannula hub assembly wherein the hub is generally cup-shaped including a tubular portion having an open end which threadably receives the tubular end portion of the pen injector and a closed end portion which receives and secures the needle cannula. The tubular portion of the needle hub may be threadably or otherwise attached to the tubular end portion of the pen injector. The needle cannula extends through the end portion of the hub and includes a first end portion which extends into the body portion of the pen injector for piercing the closure in the vial and an opposed second end portion used for injection of a patient, including self-injection.

The improved safety shield system of this invention includes a generally tubular clip member preferably having a tubular body portion received around the tubular hub portion of the needle hub assembly and a plurality of spaced laterally projecting resilient fingers. In the preferred embodiment of the safety shield system of this invention, the free ends of the resilient fingers are hook-shaped opening toward the body portion of the pen injector. The safety shield system further includes a generally tubular reciprocable shield having a first tubular portion surrounding the clip member and a second tubular portion normally surrounding the second end of the needle cannula. As described below, the shield is spring biased to normally extend the second portion of the shield around the needle cannula. The shield further includes a plurality of spaced axially extending inwardly opening channel-shaped tracks on an inner surface of the shield which receive the resilient fingers of the clip member. During reciprocal motion of the shield as described below, the axially extending channel-shaped tracks guide the shield from a first position, wherein the shield second portion surrounds the second end of the needle cannula, to a second position, wherein the second end of the needle cannula is exposed for injection of a patient. The safety shield system further includes a spring resiliently biasing the shield axially to normally extend the shield second portion to surround the second end of the needle cannula. Thus, during use of the pen injector, the health care worker or patient presses the end of the shield against the area to be injected, which retracts the shield to the second position against the force of the spring. In the most preferred embodiment, the shield is cup-shaped including the first and second tubular portions described above and a generally closed end portion having a central opening which receives the second end of the needle cannula therethrough during injection. Following use, the spring automatically extends the shield to enclose the second end of the needle cannula.

At least one of the channel-shaped tracks in the shield includes an opening spaced from but near the open end of the shield, and means is provided to prevent the free end of the resilient finger from being received in the opening during retraction of the shield from the first position enclosing the second end of the needle cannula to expose the needle cannula as described. Thus, the shield may be retracted to expose the second end of the needle cannula during injection, but the resilient finger will lock into the opening when the spring extends the shield to enclose the second end of the needle cannula following injection. The shield is thereby locked in the first position enclosing the second end of the needle cannula following injection. In the preferred embodiment, wherein the free end of the resilient fingers are hook-shaped as described above, the hook-shaped portion of the finger is received through the opening and securely locks the shield in the closed position. In the most preferred embodiment, each of the channel-shaped tracks include an opening which receives and secures each of the locking fingers. The improved safety shield system of this invention thus permits one retraction of the safety shield during injection and locks the safety shield to enclose the second end of the needle cannula following injection. Although various means may be utilized to prevent receipt of the locking fingers in the openings in the channel-shaped tracks during retraction of the safety shield to expose the needle cannula, a preferred embodiment includes a resilient detent or finger portion in the tracks adjacent the opening which resiliently biases the fingers of the clip member inwardly, such that the resilient fingers of the clip member travel past the opening during retraction of the shield member to the second position as described above. Further, the resilient detents catch the hook-shaped end portions of the resilient fingers during extension of the shield, assuring locking of the shield in the extended position following injection.

The preferred embodiment of the safety shield system of this invention further includes a removable cup-shaped cap which is received over the shield prior to use. As will be understood, the cap is then removed and the pen injector is ready for use as described above. However, the cap of the improved safety shield system of this invention may also be used to safely store and dispose of the double ended needle cannula. As described above, the second end of the needle cannula is protected following injection by the safety shield which is locked in the extended position surrounding the second end of the needle cannula. The needle cannula and safety shield system may then be safely stored in the cap for disposal by removing the needle cannula and safety shield assembly from the pen injector and inserting the first end of the needle cannula into the cup-shaped cap which is configured and adapted to receive and store the assembly for safe disposal. That is, the first end of the needle cannula is then located in the cup-shaped cap preventing exposure to the needle cannula and the second end portion is safely enclosed by the safety shield which is locked in the extended position protecting the second end of the needle cannula.

The safety shield system of this invention thus provides reliable operation and protection from the needle cannula. In the preferred embodiment, the generally tubular safety shield moves axially guided by the axially extending channel-shaped tracks as described above, thereby eliminating rotational movement of the shield or a complex track system. In the most preferred embodiment, the tubular body portion of the clip member includes a plurality of spaced axially extending radially projecting ribs which are received in axially extending grooves in the tubular portions of the shield, assuring axial movement of the shield during retraction and extension of the shield as described above. In the most preferred embodiment, the resilient fingers of the clip member include a U-shaped portion integrally connected to the tubular portion of the clip member and hook-shaped free end portions as described above. This configuration provides additional resiliency for the hook-shaped end portions of the fingers. Further, the U-shaped portion of the fingers preferably open toward the generally closed end of the shield and the spring includes a first end received in the U-shaped portions of the fingers and a second end biased against the generally closed end of the shield assuring reliable movement of the shield.

The pen needle and safety shield system of this invention also prevents retraction of the shield during assembly of the safety shield system on the pen injector. As set forth above, one problem with the prior art pen needles has been potential piercing of the cap during threaded assembly of the cap and shield assembly on the pen dispenser thereby exposing the user to puncture. The cap of the improved safety shield system includes a plurality of radially inwardly projecting ribs which are received in the axially extending grooves in the tubular portion of the shield against the axially projecting ribs on the clip member. The grooves in the tubular portion of the shield preferably extend through the side wall of the shield from adjacent the generally closed end to the ribs. These internal ribs on the cap prevent retraction of the shield during threaded assembly of the cap and shield assembly on the pen injector, thereby preventing accidental puncture during assembly.

The pen needle and safety shield system of this invention thus permits normal operation of the safety shield to retract the shield during injection and automatically extends and locks the shield following injection to prevent inadvertent contact with the second end of the needle cannula. Further, as described above, the needle cannula assembly may then be safely stored in the cup-shaped cap or cover for disposal wherein the first end of the needle cannula is located in the cup-shaped cover and the second end is protected by the safety shield. Other advantages and meritorious features of the pen needle and safety shield system of this invention will be more fully understood from the following description of the preferred embodiments, the appended claims and the drawings, a brief description of which follows.

DETAILED DESCRIPTION OF THE PREFERRED EMBODIMENTS

Figure 1:
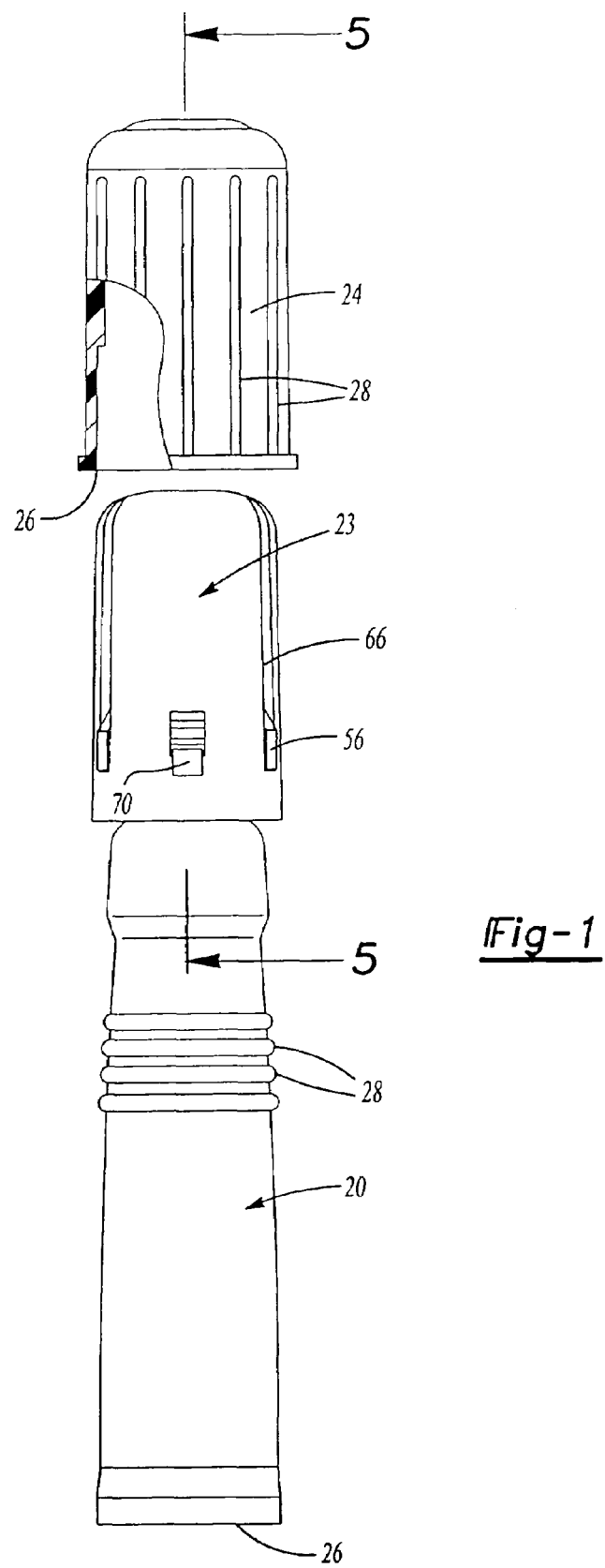
FIG. 1 is a side view of a preferred embodiment of the pen needle and safety shield system of this invention with the cap removed.
Figure 2:
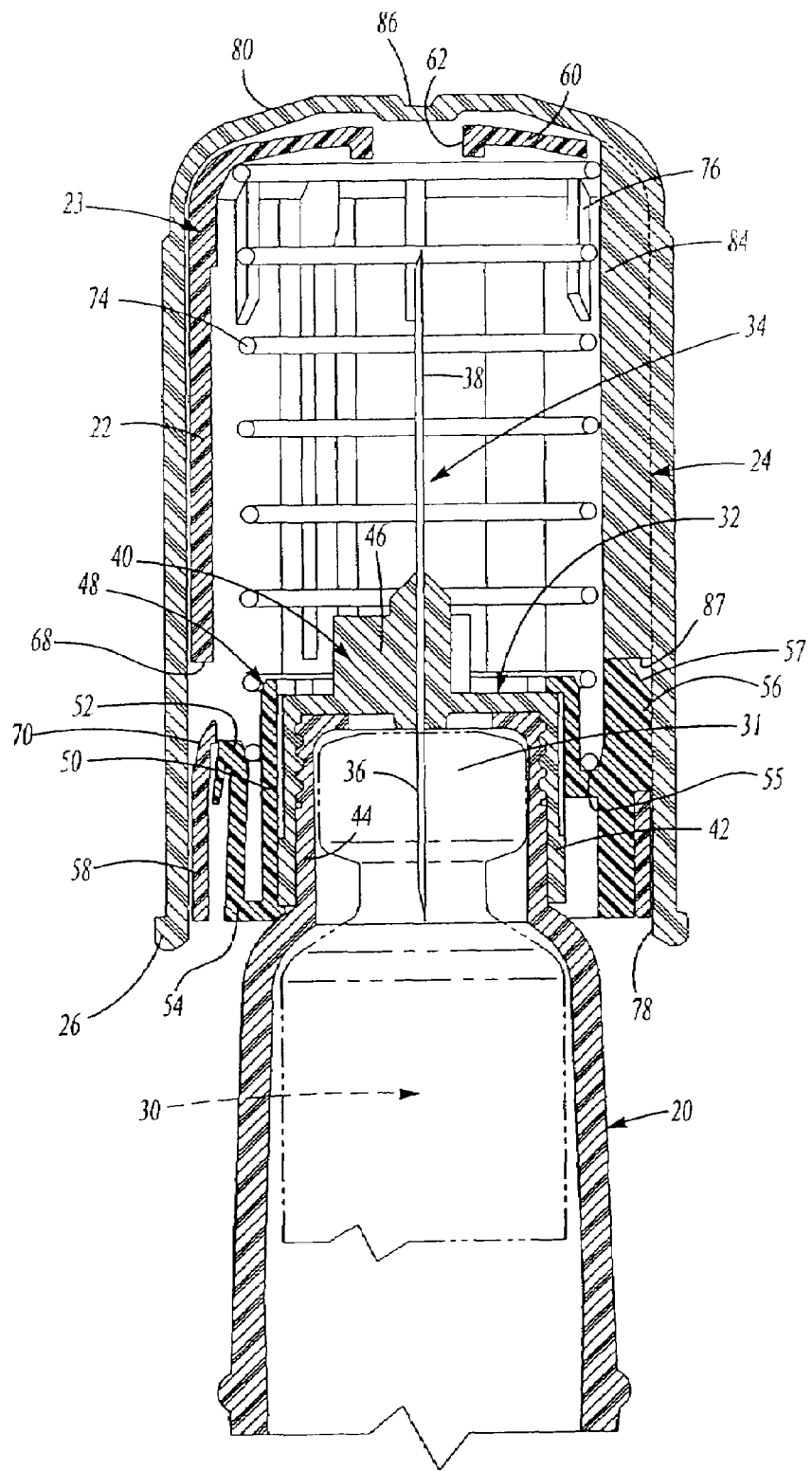
FIG. 2 is a partial cross-sectional view of the pen needle and safety shield system of this invention.
Figure 3:
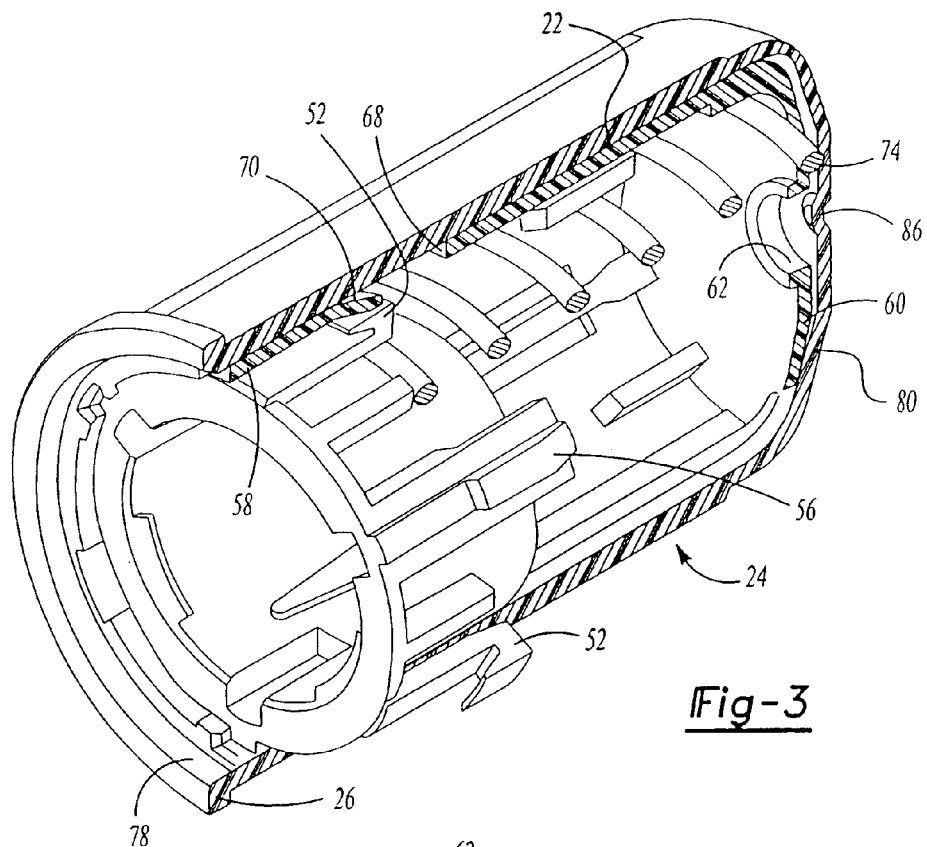
FIG. 3 is a side elevation partially cross-section of the safety shield assembly.

As set forth above, the improved safety shield system of this invention is particularly but not exclusively adapted for pen injectors, such as the pen needles available from Becton Dickinson & Company best shown at 20 in FIGS. 1 and 2. As will be understood, however, the safety shield system of this invention may also be used with other pen injectors of this general type and with conventional hypodermic syringes as described above.

As described below, the safety shield 22 normally encloses the second end 38 of the needle cannula 34 as shown in FIG. 2 and the safety shield assembly 23 is enclosed by a cup-shaped cap 24 as shown in FIG. 1. The disclosed embodiment of the safety shield assembly 23 includes an open end 26 which may include external ribs 28 to facilitate gripping of the safety shield assembly 23 by the user for threaded attachment of the assembly to the pen injector as described below. As shown in FIG. 2, the pen injector 20 receives a vial shown in phantom at 30 having a pierceable closure such as a rubber septum (not shown) in the open tubular end portion 31 of the vial. The pen injector 20 further includes a needle cannula and hub assembly 32 which includes a needle cannula 34 which extends through the hub member 40 to define a first end 36 which extends into the pen injector to pierce a closure of a vial 30 or other container and a second opposed end 38 used for injection, including self-administration as described above.

The hub 40 includes a tubular rim portion 42 which is preferably threadably received on the tubular end portion 44 of the pen injector 20 and a central portion 46 which receives and secures the needle cannula 34. As will be understood by those skilled in this art, the needle cannula 34 includes a lumen or small passage therethrough for transferring fluid in the vial 30 to the user for self-injection or administration by a health care worker and the tubular rim portion 42 of the hub 40 may include internal threads for threaded receipt of the hub on the externally threaded rim portion 44 of the pen injector. Needle cannula and hub assemblies of this general type are well known in this art and therefore no further description of the needle cannula and hub assembly or the pen injector are required.

The safety shield system of this invention includes a generally tubular clip member 48 having a tubular body portion 50 which is received around the tubular rim portion 42 of the needle hub member 40 as shown in FIG. 2 and a plurality of laterally projecting resilient hook-shaped fingers 52. The clip member may be formed of a resilient polymeric material, such as polypropylene, such that the fingers are able to flex inwardly and resiliently flex outwardly as described below. Alternatively, the clip member 48 may be formed of a metal stamping. As shown in FIG. 2, for example, the fingers 52 are supported on a U-shaped portion 54 which further improves the resiliency of the fingers as they flex inwardly and spring outwardly. The clip member further includes a plurality of circumferentially spaced radially extending ribs 56 which prevent rotational movement of the shield 22 and guide the shield during axial movement of the shield as described below.

Figure 4:
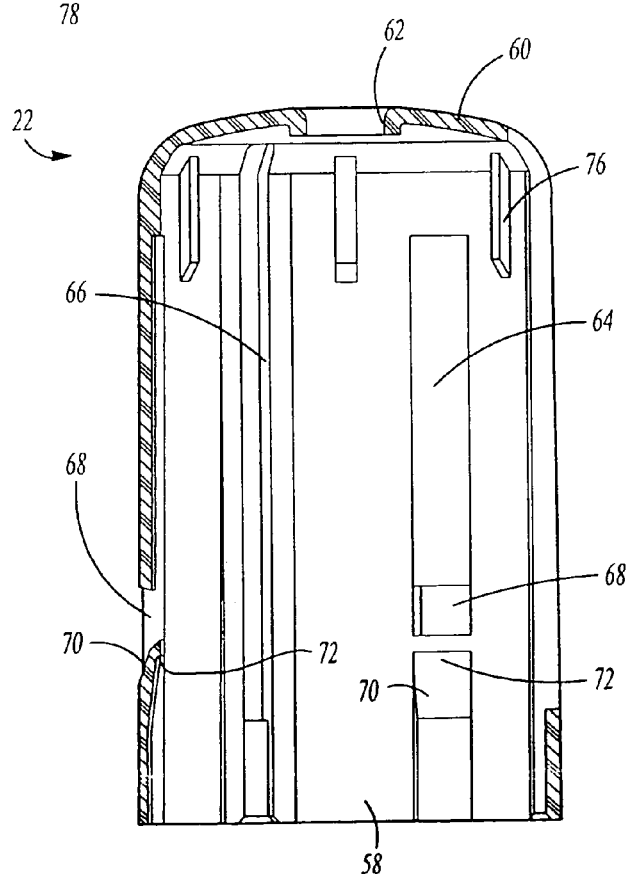
FIG. 4 is a side cross-sectional view of the safety shield.

The safety shield 22 is generally tubular having an open end 58 and preferably including a generally closed end 60 having an axial opening 62 therethrough which receives the second end 38 of the needle cannula 34 as described below. The shield 22 further includes a plurality of circumferentially spaced longitudinally or axially extending channel-shaped tracks 64 in an internal surface of the tubular portion of the shield which receives the hook-shaped fingers 52 and a plurality of circumferentially spaced axially extending slots or grooves 66 which receive the radial ribs 56 on the clip. As will be understood, the longitudinal axis of the safety shield 22 is coincident with the needle cannula 34. In the preferred embodiment, the axial channel-shaped tracks 64 each include a radial opening 68 which is generally adjacent to but spaced from the open end 58 of the shield. Each of the axial channel-shaped tracks 64 also include an inwardly projecting resilient integral tang or finger portion 70 adjacent the opening 68 closest to the open end 58 as best shown in FIG. 4. The resilient tangs or finger portions 70 resiliently bias the hook-shaped fingers 52 inwardly and preferably include a ledge 72 releasably retaining the shield 22 in the extended position prior to injection as shown in FIG. 2 and further described below.

The safety shield system of this invention further includes a coil spring 74 biased between the clip member 48 and the generally closed end 60 of the shield resiliently urging the shield toward the extended position to enclose the second end 38 of the needle cannula 34 as shown in FIG. 2. In the disclosed embodiment, the inside surface of the shield includes a plurality of circumferentially spaced radially projecting ribs 76 which centers the coil spring 74 in the shield. Finally, the cup-shaped cap 24 includes an open end 78 which receives the safety shield assembly 23 and needle cannula and hub assembly 32 as described below and a closed end 80. In the most preferred embodiment, the internal surface of the cap includes a plurality of radially projecting ribs which extend axially from adjacent the closed end 80 to the ends of the radial ribs 56 which prevent retraction of the safety shield 22 during assembly on the pen injector 20 as described below. The external surface of the cap may also include ribs 28 to assist in gripping the cap during assembly of the safety shield assembly 23 on the pen injector 20. The closed end 80 of the cap also includes an inwardly projecting dimple 86 which is received in the opening 62 of the shield centering the cap on the shield. Other details of the preferred embodiments of the safety shield assembly will be discussed below in the description of the assembly and operation of the disclosed embodiment of the pen needle and safety shield system of this invention.

First, the operation of the disclosed embodiment of the pen needle and safety shield system will now be described. One important advantage of the safety shield assembly of this invention is that the safety shield assembly 23 and the needle cannula and hub assembly 32 may be preassembled and supplied to the patient or end user as an assembly ready for use. The first step by the patient or end user is then to attach this assembly to the pen injector 20 by threading the tubular rim portion 42 of the needle hub assembly 32 on the tubular end portion 44 of the pen injector. As can be seen from FIG. 2, the internal radial ribs 84 on the cap 24 which are aligned with the ribs 56 of the clip member 48 prevent inadvertent depression or retraction of the safety shield assembly 23 which could drive the second end 38 of the needle cannula 34 through the opening 62 of the shield and puncture the cap, which would expose the end user to the needle. This is an important improvement over prior pen needle injectors where the patient or health care worker could be inadvertently exposed to the needle during assembly. The vial 30 may be previously loaded into the pen injector 20 and the open end 26 may be closed by an end cap, such that the threaded assembly results in piercing the first end 36 through the closure, such as a rubber septum, in the open end 31 of the vial 30 as the tubular rim portion 42 of the needle hub is threaded onto the rim portion 44 of the pen injector. Alternatively, the vial 30 may be inserted into the pen injector following assembly.

Figure 5:
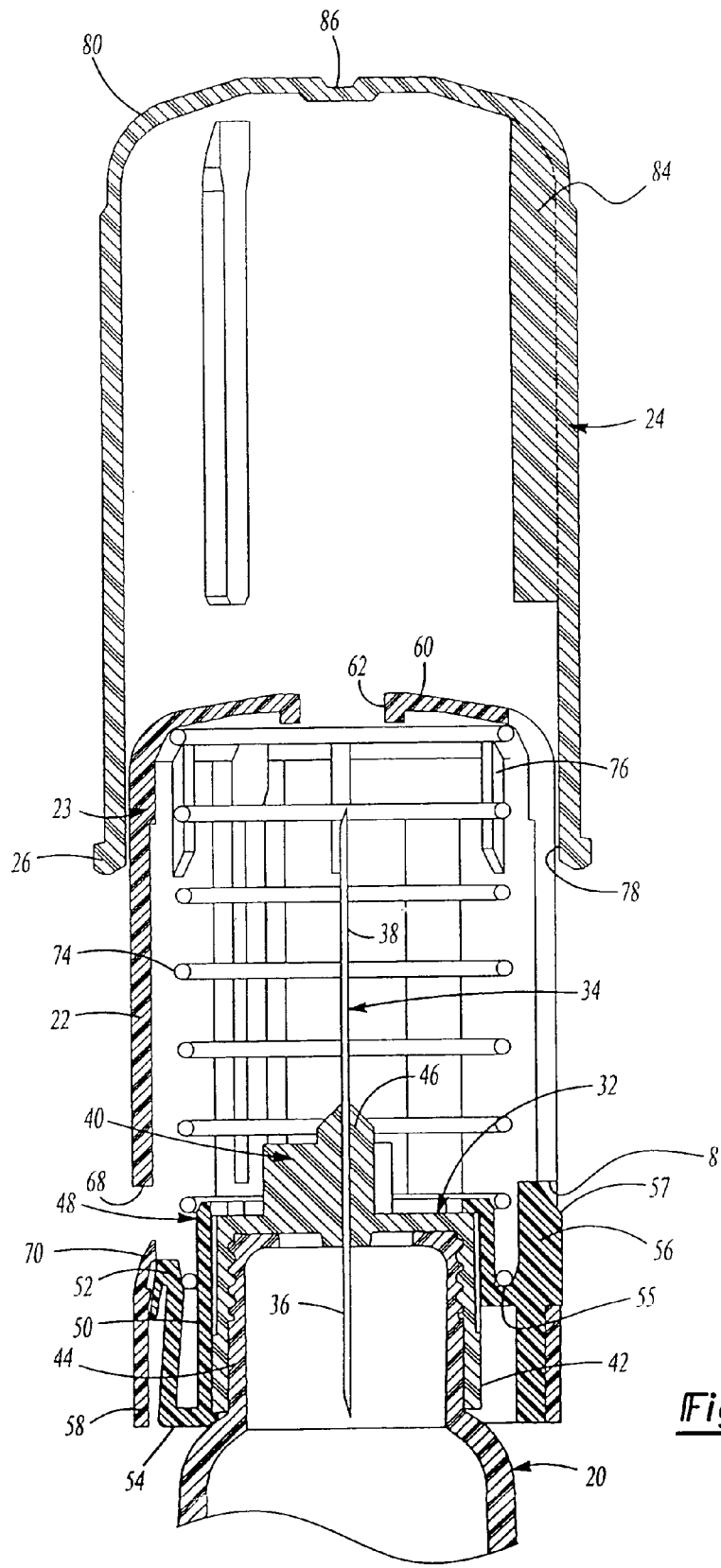
FIG. 5 is a partial side cross-sectional view of FIG. 1 in the direction of view arrows 5-5.

The cap 24 is then removed from the assembly as shown in FIGS. 1 and 5. The pen needle and safety shield assembly of this invention is then ready for use.

Figure 6:
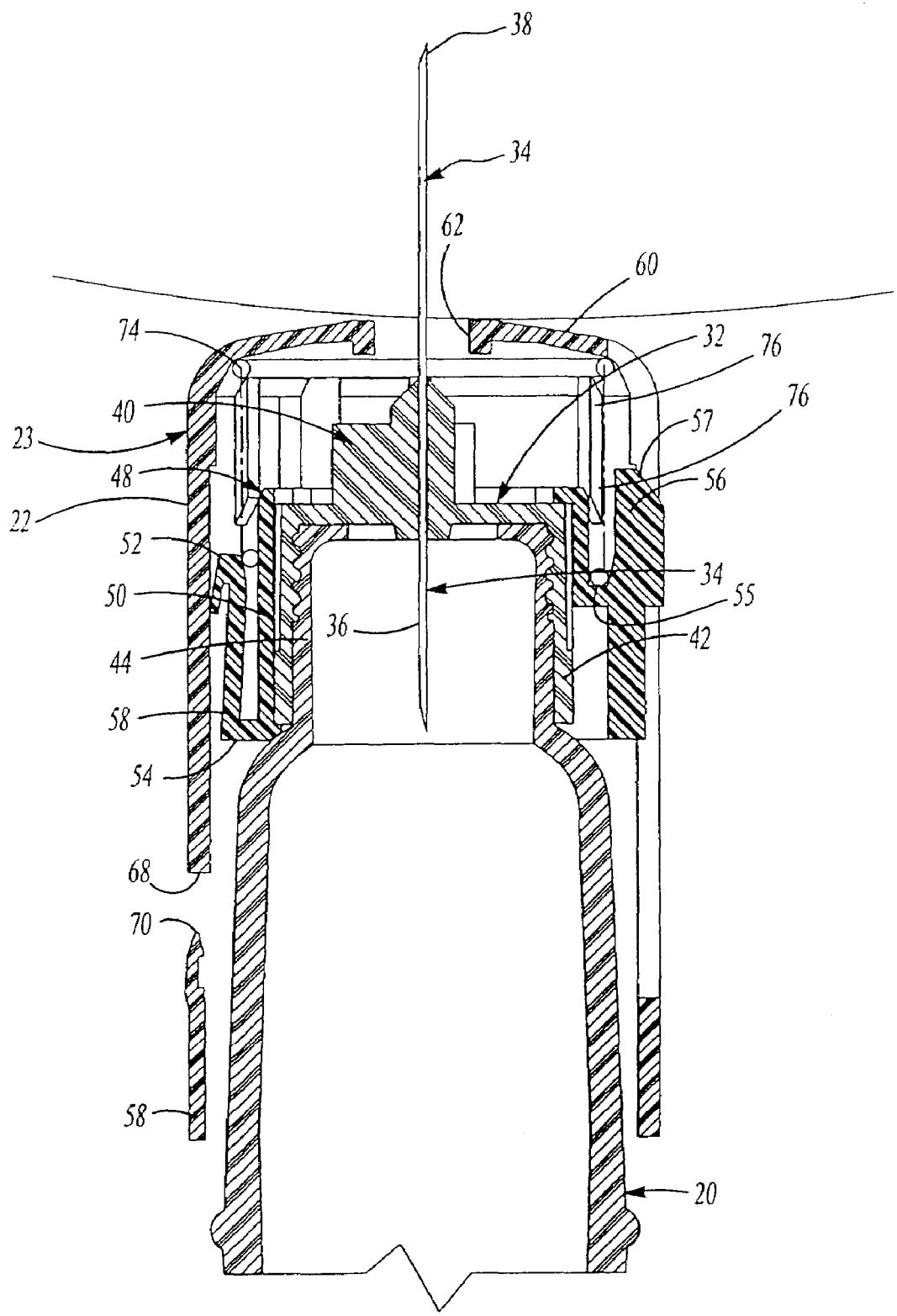
FIG. 6 is a partial cross-sectional view similar to FIG. 5 during use of the pen needle and safety shield assembly for injection.

As set forth above, the safety shield assembly 23 of this invention is particularly, but not exclusively, suitable for pen needle injectors typically used for self-administration of fluid or liquid drugs, vaccines or medicament, such as insulin, anti-histamines, et cetera. During use, the patient simply depresses the generally closed end 60 of the safety shield against the body area to be injected as shown in FIG. 6. As shown in FIGS. 2 and 5, the hook-shaped fingers 52 are releasably retained by the inwardly projecting tangs or finger portions 70 of the shield preventing inadvertent retraction of the shield and providing some resistance to movement of the shield during injection which is considered an advantageous feature of this invention. Further, the fingers 52 are resiliently biased inwardly, such that retraction of the shield when the generally closed end of the shield is pressed against the skin causes the fingers 52 to move over the openings 68 and move into the channel-shaped tracks 64 during initial retraction of the shield, exposing the second end 38 of the needle cannula which is received through the opening 62 of the shield, resulting in injection of the patient. Rotation of the shield relative to the needle cannula and hub assembly 32 is prevented by the ribs 56 which follow the axial slots or grooves 66 assuring axial movement of the shield.

Figure 7:
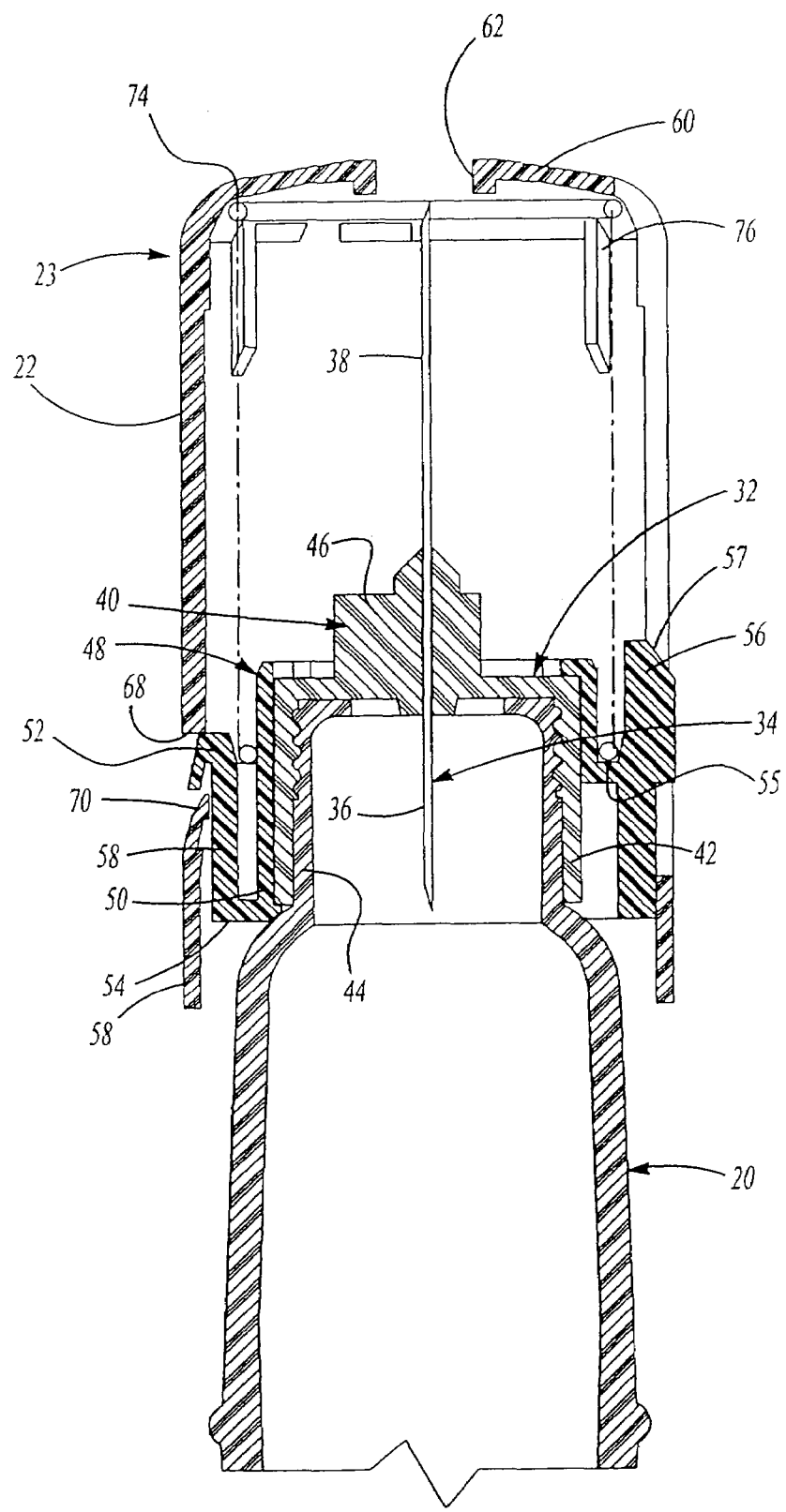
FIG. 7 is a partial side cross-sectional view similar to FIG. 6 following injection.

Following injection, the needle 38 is withdrawn from the patient and the shield 22 is simultaneously extended by the coil spring 74, such that the second end 38 of the needle cannula is never exposed. The shield is then extended axially as the needle is withdrawn because the hook-shaped fingers move in the axial channel-shaped track 64 and the radial ribs 56 move through the slots or grooves 66. However, upon full extension of the shield to enclose the second end 38 of the needle, the hook-shaped fingers 52 are received through the openings 68 and the hook-shaped portion is received around the inwardly projecting tang 70, locking the shield in the extended position as shown in FIG. 7. That is, the shield 22 cannot be retracted following injection to expose the second end 38 of the needle cannula.

Figure 8:
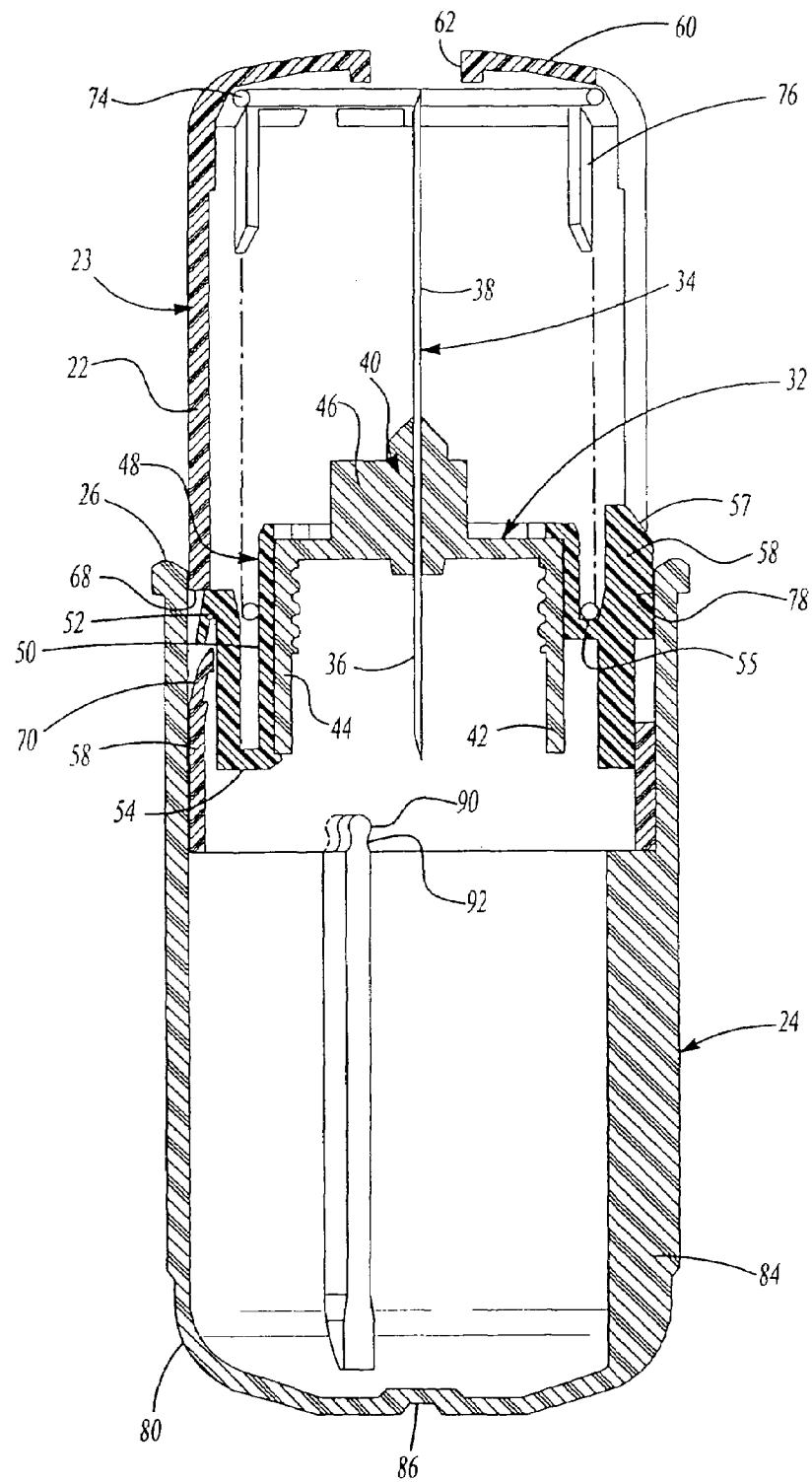
FIG. 8 is a side cross-sectional view of the safety shield system following removal from the pen injector and assembly for safe storage.

The safety shield assembly 23 may then be removed from the pen injector 20 by unthreading the tubular rim portion 42 of the hub member 40 from the threaded tubular portion 44 of the pen injector 20 and safely disposed of directly into a sharps container or by reversing this assembly and inserting the assembly into the cup-shaped cap 24 as shown in FIG. 8. The first sharp end 36 of the needle cannula is thus safely received in the cup-shaped cap 24 and the second end 38 of the needle cannula is protected by the safety shield 22, which is locked in the extended position, providing for safe disposal of the entire assembly. In the most preferred embodiment, the internal ribs 84 of the cap 24 provides an interference fit with the safety shield assembly 23, preventing inadvertent removal of the assembly from the cap and thus preventing inadvertent exposure to either end of the needle cannula 34 following disposal. In the disclosed embodiment, one or more of the ribs 84 include a ball-shaped end portion 90 which is received in a socket 92, securing the assembly in the cap 24 as shown in FIG. 8.

The improved safety shield assembly of this invention thus provides several important advantages over the prior art, particularly pen injectors. First, the safety shield assembly 23 and cap 24 may be easily attached to the pen injector 20 without inadvertent retraction of the safety shield assembly 23 on the pen injector and piercing of the cap 24, exposing the needle and the patient. This safety feature is provided by the radial ribs 56 on the hub member 40, which engage the internal ribs 84 of the cap 24 preventing retraction of the shield during assembly. Upon removal of the cap, the pen injector may be easily utilized for self-injection by the patient by depressing the generally closed end 60 of the safety shield 22 against the area to be injected without ever exposing the second end 38 of the needle cannula 34 to view. Following injection, the safety shield 22 is automatically extended by the spring to enclose the second end 38 of the needle cannula 34 and locked in the extended position by the resilient fingers 52 which extend into the openings 68 through the channel-shaped tracks 66. The hook-shaped fingers also lock over the resilient integral tangs 70. Following use, the safety shield assembly 23 and needle cannula and hub assembly 32 may be easily removed from the pen injector 20 by unthreading the tubular rim portion 42 of the hub member 40 from the tubular rim portion 44 of the pen injector, reversing the assembly, and inserting the first end 36 of the needle cannula into the cap 24, providing for safe disposal of the assembly wherein both ends of the double ended needle cannula are safely enclosed, preventing inadvertent contact with the needle.

As set forth above, the needle cannula and hub assembly 32 is assembled in the safety shield assembly 23 prior to receipt by the end user, wherein the hook-shaped fingers 52 are releasably retained by the ledge 72 of the inwardly projecting tangs 70 during assembly of the shield 22 on the clip member 48. The cap 24 is assembled on the shield by disposing the inwardly projecting radial ribs 84 of the cap into the slots 66 in the shield as best shown in FIG. 1, wherein the end portions 87 engage the ends of the radial rib portions 56 as best shown in FIG. 2. The radial ribs in the disclosed embodiment include a chamfered end 57 which guides the ribs into the slot 66 and the radial ribs are connected to the tubular body portion by web portions 55. Further, the coil spring 74 is received between the radial ribs and the tubular body portion against the web portion 55 as shown in FIG. 2. The radial ribs may thus be resiliently flexed inwardly during assembly. As set forth above, the clip member 48 may be formed of a resilient polymeric material, such as polypropylene or formed of a metal stamping. All of the components of the safety shield assembly 23 and the cap 24 are preferably formed of a sterilizable material including a polymeric material which can be injection molded. Thus, a suitable material for the cap 24, shield 22 and clip member 48 is a sterilizable polypropylene.

Having described a preferred embodiment of the pen needle and safety shield system of this invention, it will be understood that various modifications may be made to the disclosed embodiment within the purview of the appended claims. For example, other locking means for locking the shield 22 in the extended position following injection may be utilized. Further, locking means may be provided within the cap for locking the safety shield assembly 23 within the cap following removal of the safety shield assembly from the pen injector 20 and storage of the assembly in the safety cap as shown in FIG. 8, including interlocking ribs, etc. Further, certain improved features of the safety shield system of this invention may be utilized with conventional pen needle and shield assemblies, including, for example, the radial ribs 84 on the internal surface of the cap which prevent depression or retraction of the shield during assembly of the safety shield and cap on the pen injector as described above. Having described a preferred embodiment of this invention, we now claim the invention, as follows.

The invention claimed is:

1. A safety shield system for a needle cannula of a pen injector having a drug storage chamber, said safety shield system comprising:
   a mount for removably securing said safety shield system to the pen injector, said mount having the needle cannula secured thereon and the mount being removable with the safety shield system from the drug storage chamber with the needle cannula attached to the mount;
   a shield movably secured to said mount, said shield being movable between a first position, in which at least part of the needle cannula is surrounded by said shield, and a second position, in which at least part of the needle cannula is not surrounded by said shield, and a third position, in which the needle cannula is completely surrounded by said shield;
   a spring positioned between said mount and said shield for biasing said shield axially to said first and said third positions;
   a lock secured to said mount and in operative engagement with said shield to permit one-time movement of said shield from said first position to said second position, and one-time movement of said shield from said second position to said third position, said lock securing said shield in said third position following axial movement of said shield from said second position said third position without rotating the shield, said lock being non-depressible by a user so as to prevent subsequent movement of said shield out of said third position thereby locking said shield in said third position following movement of said shield from said second position to said third position.

2. A safety shield system as recited by claim 1, wherein said shield has a track defined on an inside surface thereof, said track having an opening defined through a sidewall of said shield, said track being sized and shaped to receive said lock, said lock moving in said track as said shield is moved between said first position and said second position, and between said second position and said third position.

3. A safety shield system as recited by claim 2, wherein said lock comprises a resilient finger having a free end portion that passes freely over said opening defined through said sidewall of said shield as said shield is first moved from said first position to said second position, and wherein said free end portion of said resilient finger passes into said opening when said shield is moved from said second position to said third position so as to lock said shield in said third position following movement of said shield from said second position to said third position.

4. A safety shield system as recited by claim 1, wherein said first position and said third position are the same.

5. A safety shield system as recited by claim 1, wherein said shield has a slot defined in a sidewall thereof, said slot extending over a longitudinal length of said shield.

6. A safety shield system as recited by claim 5, wherein said mount has a rib defined thereon that is sized and shaped to ride in said slot as said shield is moved between said first, said second, and said third positions.

7. A safety shield system as recited by claim 1, further comprising a removable cup-shaped cap initially received over said shield.

8. A safety shield system as recited by claim 7, wherein said cup-shaped cap is configured to receive and retain said mount after use, thereby providing for safe disposal of said safety shield system and needle cannula.

9. A safety shield system as recited by claim 3, wherein said lock has a tubular body portion and wherein said finger includes a U-shaped portion connected to said tubular body portion.

10. A safety shield system as recited by claim 1, wherein said spring is a coil spring.

11. A safety shield system as recited by claim 1, wherein said shield is generally cup-shaped having an open end disposed around said mount and a generally closed end having a central opening defined therethrough and through which needle cannula may freely pass as said shield is moved between said first, said second and said third positions.

12. A pen injector and safety shield assembly, comprising:
   a pen injector having a generally tubular body portion including an open end;
   a safety shield assembly removably securable to said open end of said generally tubular body of said pen injector, said safety shield assembly comprising:
   a mount for removably securing said safety shield system to the pen injector;
   a needle cannula secured to said mount and having a first end extending into the pen injector body, and a second end extending away from the pen injector body;
   a shield movably secured to said mount, said shield being movable between a first position, in which at least part of said needle cannula is surrounded by said shield, and a second position, in which said second end of the needle cannula is not surrounded by said shield, and a third position, in which said second end of said needle cannula is completely surrounded by said shield;
   a spring positioned between said mount and said shield for biasing said shield axially to said first position;
   a lock secured to said mount and in operative engagement with said shield to permit one-time movement of said shield from said first position to said second position, and one-time movement of said shield from said second position to said third position, said lock securing said shield in said third position following movement of said shield from said second position to said third position, said lock being non-depressible by a user so as to prevent subsequent movement of said shield out of said third position thereby locking said shield in said third position following movement of said shield from said second position to said third position, wherein the safety shield assembly, including the needle cannula secured to the mount, is removable as an assembly from the pen injector body.

13. A pen injector and safety shield assembly as recited by claim 12, wherein said shield has a track defined on an inside surface thereof, said track having an opening defined through a sidewall of said shield, said track being sized and shaped to receive said lock, said lock moving in said track as said shield is moved between said first position and said second position, and between said second position and said third position.

14. A pen injector and safety shield assembly as recited by claim 13, wherein said lock comprises a resilient finger having a free end portion that passes freely over said opening defined through said sidewall of said shield as said shield is first moved from said first position to said second position, and wherein said free end portion of said resilient finger passes into said opening when said shield is moved from said second position to said third position so as to lock said shield in said third position following movement of said shield from said second position to said third position.

15. A pen injector and safety shield assembly as recited by claim 12, wherein said first position and said third position are the same.

16. A pen injector and safety shield assembly as recited by claim 12, wherein said shield has a slot defined in a sidewall thereof, said slot extending over a longitudinal length of said shield.

17. A pen injector and safety shield assembly as recited by claim 16, wherein said mount has a rib defined thereon that is sized and shaped to ride in said slot as said shield is moved between said first, said second, and said third positions.

18. A pen injector and safety shield assembly as recited by claim 12, further comprising a removable cup-shaped cap initially received over said shield.

19. A pen injector and safety shield assembly as recited by claim 18, wherein said cup-shaped cap is configured to receive and retain said mount after use, thereby providing for safe disposal of said safety shield system and needle cannula.

20. A pen injector and safety shield assembly as recited by claim 14, wherein said lock has a tubular body portion and wherein said finger includes a U-shaped portion connected to said tubular body portion.

21. A pen injector and safety shield assembly as recited by claim 12, wherein said spring is a coil spring.

22. A pen injector and safety shield assembly as recited by claim 12, wherein said shield is generally cup-shaped having an open end disposed around said mount and a generally closed end having a central opening defined therethrough and through which needle cannula may freely pass as said shield is moved between said first, said second and said third positions.

23. A single-use safety shield system for a needle, said safety shield system comprising:
   a hub having a needle cannula secured thereon;
   a clip received around the hub and having a resilient finger that is non-depressible by a user, said clip being removably affachable to a pen injector with the hub and the needle cannula secured on the clip;
   a shield surrounding said clip and having a first opening through which said needle may pass and a second opening defined in a sidewall thereof, said shield being movable from a first position, in which said shield at least partially surrounds said needle and said resilient finger is visible through said second opening and contained within said shield, a second position, in which said needle extends through said first opening, and a third position in which said shield completely surrounds said needle;
   said finger freely passing over said second opening as said shield is moved from said first position to said second position, and said finger extending into said second opening when said shield is moved axially from said second position to said third position to thereby lock said shield in said third position without rotation of the shield so as to prevent re-use of said single-use safety shield system.

24. A single-use safety shield system as recited by claim 23, further comprising a spring for biasing said shield toward said first and said third positions.

25. A ingle-use safety shield system as recited by claim 23, wherein said resilient finger comprises a visual indicator depicting a pre-use state of said safety shield system, and a post-use state of said safety shield system.

\* \* \* \* \*